United States Patent
Cunningham

(10) Patent No.: US 8,347,687 B2
(45) Date of Patent: Jan. 8, 2013

(54) APPARATUS FOR PERFORMING DISSOLVED GAS ANALYSIS

(75) Inventor: John Cunningham, Cookstown (GB)

(73) Assignee: Kelman Limited (GB)

( * ) Notice: Subject to any disclaimer, the term of this patent is extended or adjusted under 35 U.S.C. 154(b) by 702 days.

(21) Appl. No.: 12/296,046

(22) PCT Filed: Apr. 6, 2007

(86) PCT No.: PCT/EP2007/003142
§ 371 (c)(1),
(2), (4) Date: Mar. 20, 2009

(87) PCT Pub. No.: WO2007/115807
PCT Pub. Date: Oct. 18, 2007

(65) Prior Publication Data
US 2010/0005856 A1    Jan. 14, 2010

(30) Foreign Application Priority Data
Apr. 7, 2006    (GB) .................................... 0606976.9

(51) Int. Cl.
G01N 33/30    (2006.01)
G01N 1/10     (2006.01)
G01N 21/17    (2006.01)

(52) U.S. Cl. ...................................... 73/19.11; 73/23.41

(58) Field of Classification Search ............... 73/19.01, 73/19.02, 19.1, 19.11, 23.37, 23.41, 863.31, 73/863.33, 863.86
See application file for complete search history.

(56) References Cited

U.S. PATENT DOCUMENTS

| | | | | |
|---|---|---|---|---|
| 4,112,737 A * | 9/1978 | Morgan | ........................ | 73/19.02 |
| 4,402,211 A | 9/1983 | Sugawara | | |
| 4,654,806 A * | 3/1987 | Poyser et al. | .................. | 700/292 |
| 4,764,344 A * | 8/1988 | Knab | .............................. | 422/89 |
| 5,357,781 A * | 10/1994 | Tikijian | ......................... | 73/19.1 |
| 5,365,771 A * | 11/1994 | Gysi et al. | ..................... | 73/31.03 |
| 5,400,641 A | 3/1995 | Slemon | | |
| 5,659,126 A | 8/1997 | Farber | | |
| 5,708,219 A * | 1/1998 | Scheppers et al. | ......... | 73/863.31 |
| 6,037,592 A * | 3/2000 | Sunshine et al. | .............. | 250/343 |
| 6,286,375 B1 * | 9/2001 | Ward | ......................... | 73/863.12 |
| 7,028,563 B2 * | 4/2006 | Gamache et al. | .......... | 73/863.33 |
| 7,409,849 B2 * | 8/2008 | Butler et al. | ................. | 73/19.11 |
| 7,845,208 B2 * | 12/2010 | Komura et al. | .............. | 73/19.01 |

FOREIGN PATENT DOCUMENTS

EP    0860699    8/1998

OTHER PUBLICATIONS

M.W. Sigrist, "Trace gas monitoring by laser photoacoustic spectroscopy and related techniques (plenary)," Rev. Sci. Instrum., vol. 74, No. 1, pp. 486-490, Jan. 2003.*

* cited by examiner

Primary Examiner — Lisa Caputo
Assistant Examiner — Punam Roy
(74) Attorney, Agent, or Firm — Standley Law Group LLP

(57) ABSTRACT

An apparatus for performing dissolved gas analysis on electrical insulating oil. The apparatus is connectable to a first oil source and a second oil source and has a respective sample cell for each source, an analysis cell and a gas analyser. Each sample cell is selectably connectable to said analysis cell to allow fluid communication therebetween, while the other sample cell is isolated from the analysis chamber. The apparatus allows dissolved gas analysis to be performed on samples from more than one source while minimizing the effects of cross-contamination between samples.

20 Claims, 1 Drawing Sheet

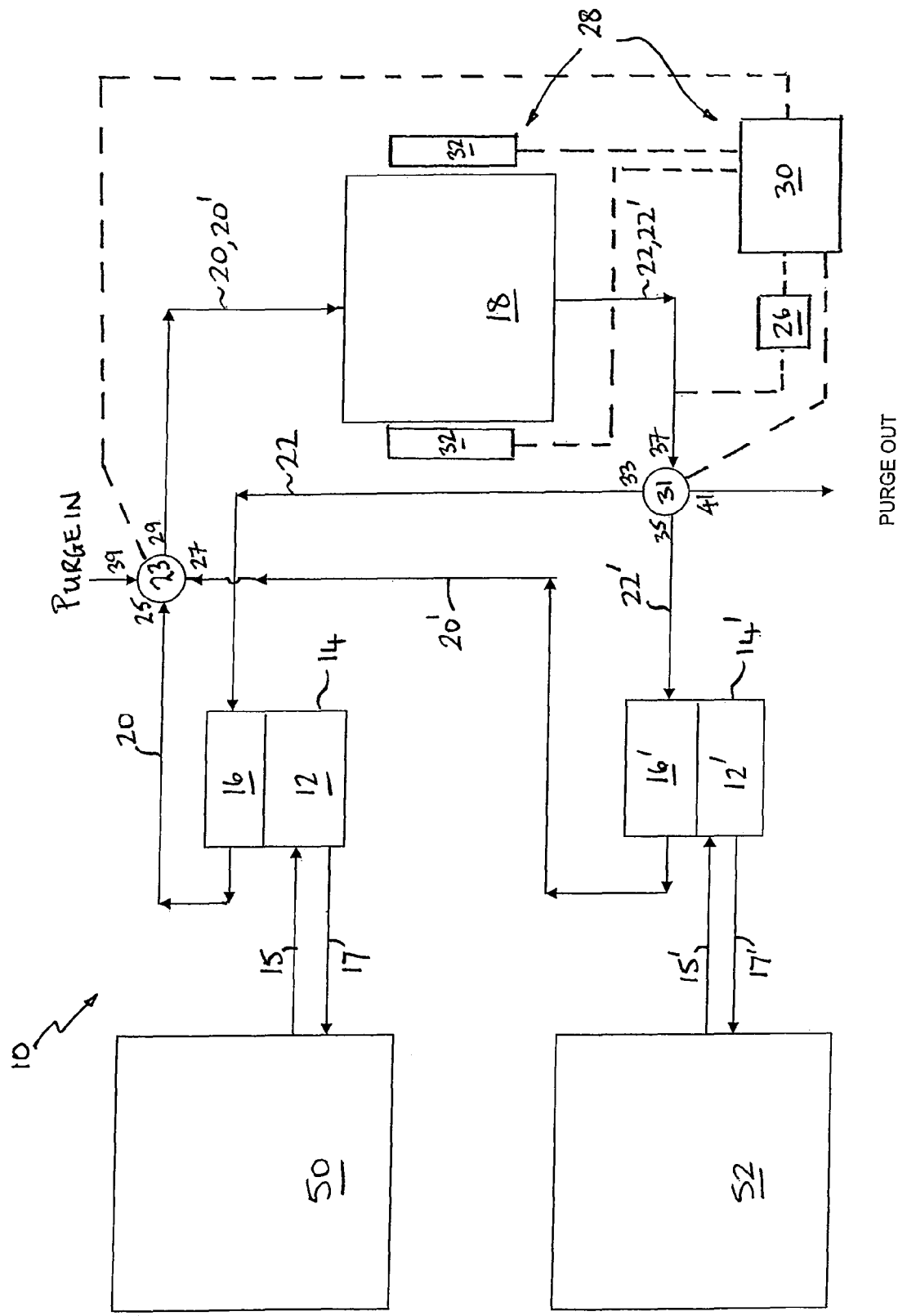

APPARATUS FOR PERFORMING DISSOLVED GAS ANALYSIS

FIELD OF THE INVENTION

The present invention relates to an apparatus for performing dissolved gas analysis, in particular the analysis of fault gases present in electrical insulating oil.

BACKGROUND TO THE INVENTION

Electrical insulating oil is commonly used in equipment for generating and distributing electrical power. Such equipment includes transformers (sometimes called oil-immersed transformers), tap-changers and circuit breakers. When a fault occurs in such equipment, fault gases may evolve in the insulating oil. Analysis of such fault gases may be used to provide a diagnosis of the operation of the electrical equipment. For example, transformer faults typically include arcing, corona discharge and overheating (pyrolysis) and it has been found that such faults can be diagnosed by analysing the quantities of certain fault gases including ethane, methane, ethylene, acetylene, carbon monoxide, carbon dioxide, hydrogen and/or oxygen that are present in the transformer oil. Such analysis can determine not only what type of faults are present, but also how severe the faults are. Accurate knowledge of the condition of electrical equipment, including transformers, is of paramount importance to electrical utilities as it allows assets to be optimised and potentially expensive failures to be avoided.

Dissolved Gas Analysis (DGA) and moisture measurement of the insulation oil are recognised as the most important tests for the condition assessment of transformers. DGA is also fast becoming the key diagnostic technique for monitoring load tap changers (LTCs).

It will be noted that the term 'gas' as used herein may embrace the term 'vapour'.

One problem associated with DGA is cross contamination between oils. As a result, measurement equipment used to perform DGA on an oil sample from one piece of equipment, say a transformer, cannot readily be used to perform DGA on an oil sample from another piece of equipment, say a tap changer, without extensive cleaning of the equipment between the respective measurements. Cleaning can be time consuming and often has to be performed off site. Alternatively, separate measuring equipment may be provided, but this is costly.

For example, convention measurement equipment tends to use a gas chromatograph to perform DGA. Graph chromatographs are relatively expensive, complex and cumbersome to use. Moreover, the operation of such equipment often requires a relatively high level of training and the processing of oil samples is slow. As a result, analysis using gas chromatograph techniques is normally performed off-site in a laboratory by suitably trained technicians. To compound this problem, gas chromatographs are relatively difficult to clean to the extent that is necessary to avoid cross-contamination.

It would be desirable to provide an apparatus for performing DGA which can measure oil samples from different sources relatively easily while minimising or avoiding cross contamination. It would also be desirable for such an apparatus to lend itself to on-line DGA analysis, i.e. analysis performed on site with the apparatus connected to the equipment, e.g. transformers and/or tap changers, from which the oil samples are extracted.

SUMMARY OF THE INVENTION

Accordingly, a first aspect of the invention provides an apparatus for performing dissolved gas analysis, the apparatus being connectable to a first oil source and a second oil source and having a respective head space, or sample, cell for each source; an analysis cell; means for selectably connecting each sample cell to said analysis cell to allow fluid communication therebetween; and means for causing fluid, especially gas, to be directed from a selected one sample cell to the analysis cell via said connecting means, while isolating the, or each, other sample cell from the analysis chamber.

In preferred embodiments, the apparatus is further connectable to a source of purging fluid, typically a gas such as air, and further includes means for causing said purging fluid to be directed into said analysis cell, and preferably also into at least part of said connecting means; and means for venting said purging fluid from the apparatus.

Typically, the connecting means includes a respective fluid conduit connecting a respective sample cell to a respective inlet of a first valve; and a common fluid conduit connecting an outlet of the first valve to the analysis cell. Similarly, the connecting means may also include a respective fluid conduit connecting a respective sample cell to a respective outlet of a second valve; and a common fluid conduit connecting an inlet of the second valve to the analysis cell. Conveniently, the first valve includes an inlet connected to said source of purging fluid. The second valve may include an outlet opening into a venting receptacle or onto the surrounding environment.

A second aspect of the invention provides a method of performing dissolved gas analysis in an apparatus of the first aspect of the invention, the method comprising causing one sample cell to be in fluid communication with the analysis cell; isolating the, or each, other sample cell from said analysis cell; causing a gas sample from said one sample cell to be introduced into said analysis cell. The method preferably also includes: isolating all sample cells from said analysis cell; and causing a purging fluid to substantially purge said analysis cell.

The invention is particularly, but not exclusively, suitable for use with target gases in the form of fault gases, e.g. ethane, methane, acetylene and ethylene, present in (normally dissolved in) electrical insulating oil, e.g. transformer oil or tap changer oil. Hence, the gas source in the headspace cell typically comprises a quantity of oil in which one or more target gases are dissolved.

In one embodiment, said first oil source comprises the main oil tank of a transformer and said second source comprises the selector tank and/or the diverter tank of a load tap changer. In alternative embodiments, there may be a plurality of oil sources, a respective sample cell being provided for each.

In preferred embodiments, the apparatus includes an analyser for measuring the quantity of a target gas in the analysis cell in the form of a spectrometer employing an infra-red (IR) or other radiation source. More preferably, the analyser comprises a photoacoustic spectrometer.

Other advantageous aspects of the invention are recited in the claims and/or will become apparent to those skilled in the art upon review of the following description of a specific embodiment of the invention.

BRIEF DESCRIPTION OF THE DRAWINGS

An embodiment of the invention is now described by way of example and with reference to the accompanying drawing, FIG. 1, which is a block diagram of an apparatus for performing DGA in accordance with one aspect of the present invention.

DETAILED DESCRIPTION OF THE DRAWINGS

Referring now to the drawing there is shown, generally indicated at 10, an apparatus for performing DGA. The apparatus 10 is connectable to at least two pieces of equipment which contain electrical insulating oil. In the drawing, the apparatus 10 is shown, by way of example, connected to two pieces of equipment, namely a transformer 50 and a tap changer 52, or load tap changer (LTC). The apparatus 10 comprises a respective sample chamber or cell 14, 14' for containing a respective oil sample 12, 12' from each piece of equipment 50, 52. Typically, the cells 14, 14' are connectable to the respective equipment 50, 52 to allow oil to be transferred between the two. To this end, it is preferred that respective forward and return lines 15, 15, 15', 17', e.g. in the form of pipes or conduits are provided between the cells 14, 14' and the equipment 50, 52. The forward lines 15, 15' allow oil to be transferred from the equipment 50, 52 to the cell 14, 14' while the return lines 17, 17' allow oil to be returned to the equipment 50, 52. In one embodiment, the apparatus 10 may be permanently connected to the equipment 50, 52 by means of said lines 15, 5', 17, 17'. In preferred embodiments, however, the lines 15, 15', 17, 17' include, or are cooperable with, means for releasable connection to the equipment 50, 52. This allows the apparatus 10 to be provided as a portable unit suitable for in-line connection to any suitable equipment.

The arrangement is such that, during use, the respective sample 12, 12' does not fill the respective sample cell 14, 14' and hence a respective headspace 16, 16' is defined within the cell 14, 14' (the sample chamber 14, 14' may be referred to as the headspace cell 14, 14'). The apparatus 10 also includes an analysis chamber or cell 18 (which may also be referred to as a measurement chamber) for containing gases and vapours extracted from each sample 12, 12' during use.

The headspace cells 14, 14' are in fluid communication with the analysis cell 18 by means of a respective fluid flow loop or circuit comprising a respective forward fluid path 20, 20' and a respective return fluid path 22, 22'. The flow circuit may be provided using any pipes or conduits that are suitable for carrying gas.

A first valve 23 is provided in the forward fluid paths 20, 20'. The valve 23 has a first inlet 25 connected to the first head space cell 14 in order to receive head space gas therefrom, a second inlet 27 connected to the second head space cell 14' in order to receive head space gas therefrom and a common outlet 29 connected to the analysis cell 18 in order to provide head space gas to the analysis cell 18 from one or other of the head space cells 14, 14' depending on the operational state of the valve 23. It will be seen, therefore, that the forward fluid paths 20, 20' are separate between the head space cells 14, 14' and the valve 23 but common between the valve 23 and the analysis cell 18.

A second valve 31 is provided in the return fluid paths 22, 22'. The valve 31 has a first outlet 33 connected to the first head space cell 14 in order to return fluid thereto, a second outlet 35 connected to the second head space cell 14' in order to return fluid thereto and a common inlet 37 connected to the analysis cell 18 in order to receive fluid therefrom. Depending on the operational state of the valve 31, fluid, typically gas, may be directed from the analysis cell 18 to either one of the head space cells 14, 14'. It will be seen, therefore, that the return fluid paths 22, 22' are separate between the head space cells 14 and the valve 31 but common between the valve 31 and the analysis cell 18.

The apparatus 10 also includes means for introducing a relatively clean or purging fluid or gas into the analysis cell 18. Conveniently, this includes means for introducing the purging fluid into the common portion of the forward fluid path 20, 20', so that it is directed into the analysis cell 18. Means for extracting the purging fluid from the cell 18 are also provided. Conveniently, this includes means for extracting the purging fluid from the common portion of the return fluid path 22, 22'. In the preferred embodiment, the valve 23 is provided with a third inlet 39 for receiving the purging fluid and the valve 23 may be set to introduce into the analysis cell 18 gas from any-one of its three inlets. Similarly, the valve 31 is provided with a third outlet 41 for venting fluid out of the return fluid path 22, 22'. The valve 31 may be set to direct fluid received from the analysis cell 18 out of any one of its three outlets. Typically, the third inlet 39 of the valve 23 is connected to a source of purging fluid, typically gas, e.g. clean air, while the third outlet 41 of the valve 31 is connected to a suitable venting receptacle or environment (not shown), e.g. may simply open onto the surrounding environment.

A conventional pump 26 is provided for causing and controlling the flow of fluid along the forward and return paths 20, 20', 22, 22' and the forward and return lines 15, 15', 17, 17'.

The apparatus 10 further comprises an analysing apparatus, generally indicated as 28, for analysing the contents of the analysis cell 18. The analyser 28 includes a control module 30 which typically comprises a microprocessor or microcontroller programmed with suitable computer software for performing analysis of the contents of the analysis cell 18 and, conveniently, controlling the operation of valves 23, 31 and pump 26.

The analysis cell 18 is typically associated with an inlet valve (not shown) for isolating it from the forward flow path 20, 20', and an outlet valve (not shown) for isolating it from the return path 22, 22'. In a typical measurement cycle, the inlet and outlet valves are opened to allow the contents of the analysis cell 18 to be flushed out by gases/vapours received from the forward flow path 20, 20'. After a suitable flushing period (typically about 15 seconds) the inlet and outlet valves are closed and the analysis cell 18 contains a new gas/vapour sample for analysis. When the inlet and outlet valves are closed, a bypass valve (not shown) is opened to allow gas/vapour to flow from the forward path 20, 20' to the return path 22, 22' bypassing the analysis cell 18. A settling time (typically about 20 seconds after the inlet and outlet valves are closed) is preferably allowed before the analyser 28 takes measurements on the new sample. The length of time taken to perform the measurements depends on the number of measurements and other operations that the analyser 28 is required to perform. In the present example, the measurements are assumed to take approximately 55 seconds. Hence, the total typical measurement cycle takes about 90 seconds. After the measurements are taken, the inlet and outlet valves are opened to begin the flushing period or purging period, as is described in more detail below.

In the preferred embodiment, the analyser 28 comprises a photoacoustic gas analyzer which, preferably, employs an infra red (IR) photoacoustic spectrometer (not shown). The PGA07 IR spectrometer as provided by PAS Technology A/S of Blokken 61, DK 3460, Denmark is a suitable device. Typically, apparatus for performing IR photoacoustic spectroscopy are relatively inexpensive, relatively compact and relatively robust and so lend themselves to being incorporated into a portable unit. Moreover, such equipment tends to be relatively easy to use (and therefore does not require a particularly skilled human operator) and to provide results relatively quickly. In the following description the invention is described in the context of IR photoacoustic spectroscopy although it will be understood that the invention is not limited to use in the context of IR spectroscopy or photoacoustic spectroscopy.

The detailed operation of an IR photoacoustic spectrometer is known. A suitable example of an IR photoacoustic spectrometer is described in United Kingdom Patent application GB 2 190 998. Typically, a radiation source, e.g. IR source, and chopper wheel (not shown) are provided to generate pulses of IR light which are then passed through a sequence of optical filters (not shown). Each filter is arranged to pass IR light in a respective frequency band associated with a particular target gas (e.g. one filter for ethane, one for methane, etc.). Although not shown in the drawing, in the preferred embodiment, the analyzer 28 therefore also includes a radiation source with associated optical filter(s) arranged to direct radiation into the analysis cell 18 via a window (not shown) in the chamber 18. The pulses of filtered IR light then pass through the analysis cell 18 which contains a quantity of gas to be analysed. Each particular target gas absorbs energy at its respective resonant frequency, causing a vibration in the molecules of that gas. The absorbed energy is quickly released creating pressure waves. One or more microphones 32 (typically two) are provided adjacent the cell 18 to detect the pressure waves. The amplitude of the respective detected pressure waves may be used to determine the quantity of the respective target gases.

In use, a respective sample 12, 12' is drawn into the respective sample cells 14, 14' from the equipment 50, 52. The samples 12, 12' are agitated by means of a conventional agitator (not shown) to cause dissolved gasses to be released from the samples 12, 12' into the respective head space 16, 16'. After a period of agitation, head space equilibrium is achieved—this is when the respective quantities of gasses in the head space 16, 16' have stabilised. Before measurement of the head space gasses is performed, it is preferred to cause the analyser 28 to measure the natural gas concentrations in the analysis cell 18 (and preferably also the surrounding pipe work 20, 22). This allows background gas concentrations to be calculated and this information can be used to more accurately analyse the head space gases. In order to analyse the head space gases, the control module 30 causes, by appropriate control of the valves 23, 31, a quantity of the head space gas from one of the cells 14, 14' to be directed into the analysis cell 18 as well as establishing a return connection from the analysis cell 18 to said one head space cell 14, 14', i.e. a flow loop or circuit is established from one cell 14, 14' to the analysis cell 18 and back to said one cell 14, 14'. The inlet and outlet valves of the analysis cell 18 may then be closed to capture a sample. Hence, a sample of head space gas from said one cell 14, 14' can be captured and analysed in the analysis cell 14, 14'. Similarly, by appropriate alternate control of the valves 23, 31, a sample head space gas from the other cell 14', 14 can be captured and analysed in the analysis cell 14, 14'. Depending on the measurement technique being used, the valve 31 may be set to return gas from the analysis cell 18 to the respective head space cell 14, 14' (closed loop measurement) or to cause the gas from the analysis cell 18 to be vented out of the flow circuit 22, 22' (open loop measurement). Measurements taken in the analysis cell 18 can be taken when both the inlet and outlet valves of the cell 18 are closed, or when one or both of said inlet and outlet valves are open, depending on which measurement technique is used. In cases where only open loop type measurements are required, the return paths 22, 22 are not required and can be omitted. Moreover, measurements may be taken before, during and/or after headspace equilibrium is reached.

The respective head space gas captured in the analysis cell 18 for measurement is usually obtained from the respective heads space 16, 16' after head space equilibrium is reached. However, depending on the measurement techniques being used, head space gas may be measured before equilibrium is reached.

After the head space gas from one cell 14, 14' has been measured, it may be desirable to cleanse or purge the analysis cell 18 (and typically also the common fluid paths 20, 20', 22, 22' connected thereto) before measuring the head space gas from the other cell 14', 14. By appropriate setting of the valves 23, 31, the control module 30 causes purging fluid, typically gas, e.g. clean air, to be drawn into the forward flow path 20, 20' at valve 23, directed through the analysis cell 18, into the common return path 22, 22' and out of the flow circuit at valve 31. Once purging is complete, the valves 23, 31 may be reset to draw head space gas from and recirculate head space gas to one or other of the cells 14, 14'.

The apparatus 10 may be said to comprise a headspace system. The embodiment of the invention described and illustrated herein is presented in the context of the analysis of fault gases in electrical insulating oil (and more specifically transformer oil) but the invention is not limited to such. More generally, one aspect of the invention relates to the analysis of one or more target gases in a headspace system in which one or more interferents are present. The invention is particularly, but not exclusively, suitable for use in the measurement of ethylene, acetylene, ethane and/or methane.

In alternative embodiments, not illustrated, the apparatus 10 may be connectable to more than two pieces of equipment, a respective head space cell being provided for each and the valves 23, 31 having a corresponding number of inlet/outlets to allow gas to be drawn from and recirculated to a respective one head space cell at a time. Further, each head space cell may be connectable to more than one source of oil, or more than one piece of equipment, in cases where cross contamination is not a concern. For example, a single head space cell may be connected to both an LTC selector tank and an LTC diverter tank (by means of a suitable valve system to allow oil to be drawn/returned to one or other of the sources).

In an alternative embodiment (not illustrated) a respective separate forward flow path and/or return flow path may be provided between the respective head space cells 14, 14' and the analysis cell 18, i.e. there may be no common portion of the flow and/or return path. This may be achieved by, for example, providing a multi-inlet, single-outlet valve (e.g. similar to valve 23) at the inlet and/or a single-inlet, multi-outlet valve (e.g. similar to valve 31) at the outlet of the measuring chamber 18, to which the conduits of the respective forward paths, return paths and purge channels can be connected as applicable. Alternatively, a respective separate valve, as required, may be provided at the inlet and/or outlet of the analysis cell 18 for each flow path and/or return path and/or purge channel.

The apparatus is particularly, but not exclusively, suited for use in taking on line measurement from a main transformer tank and from the tap changer (e.g. LTC selector tank and/or LTC diverter tank). This is because tap changer oil has very large concentrations of combustible gases dissolved in the oil whereas main tank oil in general has much lower levels of gas in the oil. Hence the risk of cross contamination is high.

The apparatus 10 can measure accurately the tap changer gases, and so key ratios of say ethylene to acetylene can be determined accurately. This allows an on line diagnosis of Tap Change contact condition to be given.

Hence, preferred embodiments afford reliable on-line DGA of the main tank and the LTC giving vital, real-time insight into the condition of the whole transformer system. Moreover, transformer and LTC faults can be detected in their infancy, minimising costly unplanned outages and equipment failure. No consumable carrier or calibration gases are required and minimal maintenance and running costs are incurred.

The invention is not limited to the embodiments described herein which may be modified of varied without departing from the scope of the invention.

The invention claimed is:

1. An apparatus for performing dissolved gas analysis, the apparatus being connectable to a first oil source and a second oil source, the apparatus comprising a respective sample cell for each source; an analysis cell; an analyser for performing gas analysis on a quantity of gas contained, in use, in said analysis cell; at least one fluid conduit configured to provide for each sample cell a respective fluid flow path from the respective sample cell to said analysis cell and a respective fluid return path, separate from the respective fluid flow path, from the analysis cell to the respective sample cell; and at least one valve configurable to selectably connect each sample cell to said analysis cell to allow fluid communication therebetween by the respective fluid flow path and the respective fluid return path; and a controller operable to control said at least one valve to cause gas to be circulated between a selected one of said sample cells and said analysis cell by the respective fluid flow path and the respective fluid return path, while isolating the, or each, other of said sample cells from said analysis cell.

2. An apparatus as claimed in claim 1, the apparatus being connectable to a source of purging fluid, and further including means for causing said purging fluid to be directed into said analysis cell.

3. An apparatus as claimed in claim 2, further including means for venting said purging fluid from the apparatus.

4. An apparatus as claimed in claim 1, wherein said at least one fluid conduit and said at least one valve are arranged to provide a respective fluid flow path from an outlet of each sample cell to an inlet of the analysis cell, wherein said at least one fluid conduit comprises respective separate fluid conduits providing at least part of said respective fluid flow paths.

5. An apparatus as claimed in claim 4, wherein said at least one fluid conduit includes a common fluid conduit connected to the inlet of said analysis cell, said common fluid conduit being common to each of said respective fluid flow paths.

6. An apparatus as claimed in claim 1, wherein said at least one fluid conduit and said at least one valve are arranged to provide a respective fluid return path from an outlet of said analysis cell to a respective inlet of each sample cell, wherein said at least one fluid conduit comprises respective separate fluid conduits providing at least part of said respective fluid return paths.

7. An apparatus as claimed in claim 6, wherein said at least one fluid conduit includes a common fluid conduit connected to the outlet of said analysis cell, said common fluid conduit being common to each of said respective fluid flow paths.

8. An apparatus as claimed in claim 1, wherein said at least one valve includes a first valve having a respective inlet connected to each sample cell, and an outlet connected to an inlet of said analysis cell, the first valve being operable to cause one or other of said first valve inlets to be in fluid communication with said first valve outlet.

9. An apparatus as claimed in claim 8, wherein the apparatus is connectable to a source of purging fluid, and further includes means for causing said purging fluid to be directed into said analysis cell, and wherein the apparatus is connectable to a source of purging fluid.

10. An apparatus as claimed in claim 1, wherein said at least one valve includes a second valve having a respective outlet connected to each sample cell, and an inlet connected to an outlet of said analysis cell, said valve being operable to cause one or other of said second valve outlets to be in fluid communication with said valve inlet.

11. An apparatus as claimed in claim 10, the apparatus being connectable to a source of purging fluid, and further including means for causing said purging fluid to be directed into said analysis cell, wherein the second valve includes an outlet opening into a venting receptacle or onto a surrounding environment.

12. An apparatus as claimed in claim 1, wherein said at least one fluid conduit includes a bypass conduit arranged to provide a fluid bypass around said analysis cell, the apparatus further including at least one valve for selectably directing fluid into said analysis cell or into said bypass conduit.

13. An apparatus as claimed in claim 1, wherein said analyser comprises a photoacoustic gas analyser.

14. An apparatus as claimed in claim 1, wherein said first oil source is the main oil tank of an electrical transformer.

15. An apparatus as claimed in claim 1, wherein said second source is the selector tank and/or the diverter tank of a load tap changer.

16. An apparatus as claimed in claim 1, wherein each sample cell is configured for connection to a respective one of said first and second oil sources, said apparatus further including a pump operable to draw oil into each sample cell from the respective one of said first and second oil sources or to return oil from each sample cell to the respective one of said first and second oil sources.

17. A method of performing dissolved gas analysis in an apparatus that is connectable to a first oil source and a second oil source, the apparatus comprising a respective sample cell for each source; an analysis cell; an analyser for performing gas analysis on a quantity of fluid contained, in use, in said analysis cell; at least one fluid conduit and at least one valve configured to selectably connect each sample cell to said analysis cell to allow fluid communication therebetween; and a controller configured to control said at least one valve to cause fluid to be directed from a selected one of said sample cells to said analysis cell, while isolating the, or each, other of said sample cells from said analysis cell, the method comprising: causing oil from a respective one of said first and second oil samples to partly fill at least one of said sample cells; agitating said oil to cause gas to gather in said at least one of said sample cells; causing one sample cell of said at least one sample cells to be in fluid communication with the analysis cell; isolating the, or each, other sample cell from said analysis cell; causing a gas sample from said one sample cell to be introduced into said analysis cell; and performing gas analysis on said gas sample in the analysis cell.

18. A method as claimed in claim 17, further including isolating all sample cells from said analysis cell; and causing a purging fluid to substantially purge said analysis cell.

19. A method as claimed in claim 17, further including, in a first mode of operation, causing said one sample cell to be in fluid communication with the analysis cell; isolating the, or each, other sample cell from said analysis cell; and causing said gas to circulate between said one sample cell and said analysis cell; and in a second mode of operation, causing a gas sample from said one sample cell to be held in said analysis cell; and performing gas analysis on said gas sample in the analysis cell.

20. An apparatus for performing dissolved gas analysis, the apparatus being connectable to a first oil source and a second oil source, the apparatus comprising a respective sample cell for each source; an analysis cell; an analyser for performing gas analysis on a quantity of fluid contained, in use, in said analysis cell; at least one fluid conduit and at least one valve to selectably connect each sample cell to said analysis cell to allow fluid communication therebetween; and a controller configured to control said at least one valve to cause fluid to be directed from a selected one of said sample cells to said analysis cell, while isolating the, or each, other of said sample cells from said analysis cell, wherein each sample cell is configured for connection to a respective one of said first and second oil sources, said apparatus further including a pump operable to draw oil into each sample cell from the respective one of said first and second oil sources or to return oil from each sample cell to the respective one of said first and second oil sources.

* * * * *